US008962571B2

(12) United States Patent
Maes et al.

(10) Patent No.: US 8,962,571 B2
(45) Date of Patent: *Feb. 24, 2015

(54) METHOD FOR REPAIRING DNA DAMAGE IN KERATINOCYTES

(75) Inventors: Daniel H. Maes, Huntington, NY (US); Nadine A. Pernodet, Huntington, NY (US); Lenny Slutsky, Hauppauge, NY (US); Donald F. Collins, Plainview, NY (US); Kerri Goldgraben, Commack, NY (US); Edward Pelle, Valley Stream, NY (US); James Timothy McCarthy, Babylon, NY (US)

(73) Assignee: ELC Management, New York, NY (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/452,415

(22) Filed: Apr. 20, 2012

(65) Prior Publication Data

US 2012/0219537 A1   Aug. 30, 2012

Related U.S. Application Data

(63) Continuation of application No. 12/367,705, filed on Feb. 9, 2009, now Pat. No. 8,193,155.

(51) Int. Cl.
*A61K 38/06* (2006.01)

(52) U.S. Cl.
USPC ....... 514/21.9; 514/21.5; 514/21.6; 514/21.7; 514/21.8; 514/18.6

(58) Field of Classification Search
USPC ............ 514/21.9, 21.5, 21.6, 21.7, 21.8, 18.6
See application file for complete search history.

(56) References Cited

U.S. PATENT DOCUMENTS

| | | | |
|---|---|---|---|
| 3,215,724 A | 11/1965 | Strobel et al. |
| 3,439,088 A | 4/1969 | Edman |
| 3,781,417 A | 12/1973 | Welters et al. |
| 3,818,105 A | 6/1974 | Coopersmith et al. |
| 4,003,966 A | 1/1977 | Napier et al. |
| 4,464,362 A | 8/1984 | Kludas et al. |
| 4,677,152 A | 6/1987 | Allen et al. |
| 4,702,844 A | 10/1987 | Flesher et al. |
| 4,970,252 A | 11/1990 | Sakuta et al. |
| 5,077,211 A | 12/1991 | Yarosh |
| 5,190,762 A | 3/1993 | Yarosh |
| 5,236,986 A | 8/1993 | Sakuta |
| 5,272,079 A | 12/1993 | Yarosh |
| 5,296,231 A | 3/1994 | Yarosh |
| 5,302,389 A | 4/1994 | Kripke et al. |
| 5,412,004 A | 5/1995 | Tachibana et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,843,193 A | 12/1998 | Hawkins et al. |
| 6,270,780 B1 | 8/2001 | Carson et al. |
| 6,414,037 B1 | 7/2002 | Pezzuto et al. |
| 6,572,882 B1 | 6/2003 | Vercauteren et al. |
| 6,730,308 B1 | 5/2004 | Sefton |
| 7,758,878 B2 | 7/2010 | Scimeca et al. |
| 7,842,670 B2 | 11/2010 | Dal Farra et al. |
| 8,193,155 B2 | 6/2012 | Maes et al. |
| 8,877,713 B2 | 11/2014 | Dal Farra et al. |
| 2002/0086042 A1 | 7/2002 | Delrieu et al. |
| 2002/0173472 A1 | 11/2002 | Pezzuto et al. |
| 2003/0223982 A1 | 12/2003 | Schlotmann et al. |
| 2004/0057917 A1 | 3/2004 | Wolf et al. |
| 2004/0116386 A1 | 6/2004 | Pifferi et al. |
| 2004/0142007 A1 | 7/2004 | Moussou et al. |
| 2004/0161408 A1 | 8/2004 | Lee et al. |
| 2006/0002884 A1 | 1/2006 | Golz-Berner et al. |
| 2006/0034875 A1 | 2/2006 | Nakanishi et al. |
| 2006/0165641 A1 | 7/2006 | Pillai et al. |
| 2006/0257386 A1 | 11/2006 | Zimmerman et al. |
| 2006/0257509 A1 | 11/2006 | Zimmerman et al. |
| 2006/0269616 A1 | 11/2006 | Giampapa |
| 2007/0110686 A1 | 5/2007 | Lowe et al. |
| 2007/0243148 A1 | 10/2007 | Andre et al. |
| 2007/0254021 A1 | 11/2007 | Scimeca et al. |
| 2008/0095866 A1 | 4/2008 | Declercq et al. |
| 2008/0107613 A1 | 5/2008 | Hultsch et al. |
| 2008/0274456 A1 | 11/2008 | Yankner et al. |
| 2009/0028895 A1 | 1/2009 | Smith |
| 2009/0035243 A1 | 2/2009 | Czarnota et al. |
| 2009/0047309 A1 | 2/2009 | Maes et al. |
| 2009/0082278 A1 | 3/2009 | Dal Farra et al. |
| 2009/0130139 A1 | 5/2009 | Mekideche |
| 2010/0028317 A1 | 2/2010 | Maes et al. |
| 2010/0080845 A1 | 4/2010 | Maes et al. |

(Continued)

FOREIGN PATENT DOCUMENTS

| | | |
|---|---|---|
| DE | 202004012807 | 11/2004 |
| EP | 1634576 | 3/2006 |

(Continued)

OTHER PUBLICATIONS

Kunieda, Circulation Research 102(5), 607-614, 2008.*
Asher et al., SIRT1 Reguates Circadian Clock Gene Expression through PER2 Deacetylation; Cell 134, 317-328, Jul. 25, 2008.
Biochemistry Abstract CD, 2008, 1P-1019.
Krutmann, et al.; Modern Photoprotection of Human Skin; Skin Aging; Gilchrest, B.A.; Krutmann, J.; Ed. Springer-Verlag; Berlin Heidelberg; Ch. 9; pp. 103-112; 2006.
PCT International Search Report; International Application No. PCT/US2008/071061; Completion Date: Jan. 29, 2009; Date of Mailing: Jan. 29, 2009.

(Continued)

*Primary Examiner* — David Lukton

(74) *Attorney, Agent, or Firm* — Julie M. Blackburn

(57) ABSTRACT

A method for repairing DNA damage in human keratinocytes by applying to the keratinocytes a composition comprising at least one CLOCK or PER1 gene activator and at least one DNA repair enzyme.

20 Claims, 3 Drawing Sheets

(56) References Cited

U.S. PATENT DOCUMENTS

| | | | |
|---|---|---|---|
| 2011/0243983 | A1 | 10/2011 | Paufique |
| 2011/0250251 | A1 | 10/2011 | Maes et al. |
| 2012/0027703 | A1 | 2/2012 | Dal Farra et al. |
| 2012/0093745 | A1 | 4/2012 | Dal Farra et al. |

FOREIGN PATENT DOCUMENTS

| | | |
|---|---|---|
| EP | 1 642 560 | 4/2006 |
| JP | 2002-326905 | 11/2002 |
| JP | 2004-517844 | 6/2004 |
| JP | 2004-532790 | 10/2004 |
| JP | 2005-532375 | 10/2005 |
| JP | 2007-508320 | 5/2007 |
| JP | 2008-517972 | 5/2008 |
| KR | 10-2007-0079933 | 8/2007 |
| RU | 2128504 | 4/1999 |
| WO | WO99/57137 | 11/1999 |
| WO | WO01/91695 | 12/2001 |
| WO | WO03/025151 | 3/2003 |
| WO | WO-2004024798 | 3/2004 |
| WO | WO-2005/034891 | 4/2005 |
| WO | WO2005/034891 | 4/2005 |
| WO | WO2006/029484 | 3/2006 |
| WO | WO-2006/053699 | 5/2006 |
| WO | WO2007/104867 | 9/2007 |
| WO | WO-2010/122245 | 10/2010 |

OTHER PUBLICATIONS

PCT Written Opinion of the International Searching Authority; International Application No. PCT/US2008/071061; Completion Date: Jan. 29, 2009; Mailing Date: Jan. 29, 2009.

PCT International Search Report; International Application No. PCT/US2010/023435; Completion Date: Dec. 10, 2010; Date of Mailing: Dec. 10, 2010.

PCT Written Opinion of the International Searching Authority; International Application No. PCT/US2010/023435; Completion Date: Dec. 10, 2010; Mailing Date: Dec. 10, 2010.

Collis, et al.; Emerging links between the biological clock and the the DNA damage response; Chromosoma; 116; pp. 331-339; 2007.

Gery, et al.; The Circadian Gene Per1 Plays and Important Role in Cell Growth and DNA Damage Control in Human Cancer Cells; Molecular Cell; 22; pp. 375-382; May 2006.

Fishel, et al.; The DNA base excision repair protein Ape1/Ref-1 as a therapeutic and chemopreventive target; Molecular Aspects of Medicine; vol. 28; pp. 375-395; May 2007.

PCT International Search Report; International Application No. PCT/US10/037871; Completion Date: Dec. 31, 2010; Date of Mailing: Jan. 3, 2011.

PCT Written Opinion of the International Searching Authority; International Application No. PCT/ US10/037871; Completion Date: Dec. 31, 2010; Date of Mailing: Jan. 3, 2011.

Supplementary European Search Report; EP08782328.2; Completion Date: Feb. 23, 2011; Date of Mailing: Mar. 1, 2011.

Yamaguchi, et al.; Melanin mediated apoptosis of epidermal cells damaged by ultraviolet radiation: factors influencing the incidence of skin cancer; Arch. Dermatol. Res.; 300 (Suppl 1):S43-S50; 2008.

Chua, et al.; Mammalian SIRT1 limits replicative life span in response to chronic genotoxic stress; Cell Metabolism; vol. 2; pp. 67-76; Jul. 2005.

Langley, et al.; Human SIR2 deacetylates p53 and antagonizes PML/p53-induced cellular senescence; The EMBO Journal; vol. 21; No. 10; pp. 2383-2396; 2002.

Kuningas, et al.; SIRT1 Gene, Age-Related Diseases, and Mortality: The Leiden 85-Plus Study; The Journals of Gerontology Series A: Biological Sciences and Medical Sciences; 62:960-965; http://biomed.gerontologyjounrals.org/cgi;content/abstract/62/9/960; 2007.

Bjarnason, et al.; Circadian variation of cell proliferation and cell cycle protein expression in man: clinical implications.; Prog Cell Cycle Res.; 4:193-206; http://www.ncbi.nlm.nih.gov/pubmed/10740826?dopt=Abstract; 2000.

Agar, et al.; Melanogenesis: a photoprotective response to DNA damage?; Mutation Research; 571 (1-2):121-32; http://www.ncbi.nlm.nih.gov/pubmed/15748643; Epub Jan. 23, 2005; Apr. 2005.

Dickmeis, Thomas; Glucocorticoids and the circadian clock; Review; Journal of Endocrinology; Circadian rhythms and glucocorticoids; 200; pp. 3-22; www.endocrinology-journals.org; 2009.

Nagoshi, et al.; Circadian Gene Expression in Individual Fibroblasts: Cell-Autonomous and Self-Sustained Oscillators Pass Time to Daughter Cells; Cell; vol. 119; pp. 693-705; Nov. 2004.

Kawara, Shigeru, et al.; Low-dose Ultraviolet B Rays Alter the mRNA Expression of the Circadian Clock Genes in Cultured Human Keratinocytes; The Journal of Investigative Dermatology; vol. 119, No. 6; pp. 1220-1223; Dec. 2002.

Sosniyenko, Serhiy, et al.; Influence of photoperiod duration and light-dark transitions on entrainment of Per1 and Per 2 gene and protein expression in subdivisions of the mouse suprachiasmatic nucleus; The European Journal of Neuroscience; vol. 30, No. 9; pp. 1802-1814; Nov. 2009; Blackwell Science, Paris.

Dryden, et al.; Role for Human SIRT2 NAD-Dependent Deacetylase Activity in Control of Mitotic Exit in the Cell Cycle; Molecular and Cellular Biology; vol. 23; No. 9; pp. 3173-3185; May 2003.

Zanello, et al.; Expression of the Circadian Clock Genes clock and period 1 in Human Skin; The Journal of Investigative Dermatology; Circadian Gene Expression in Skin; vol. 115; No. 4; Oct. 2000.

Ünsal-Kaçmaz; Coupling of Human Circadian and Cell Cycles by the Timeless Protein; Molecular and Cellular Biology; vol. 25; No. 8; pp. 3109-3116; Apr. 2005.

Clayton, et al.; Keeping time with the human genome; Analysis; Nature; Dept. of Genetics, University of Leicester, Leicester UK; vol. 409; pp. 829-831; www.nature.com; Feb. 2001.

Hunt, et al.; Riding Tandem: Circadian Clocks and the Cell Cycle; Leading Edge; Minireview; Cell; 129; pp. 461-464; May 2007.

Yarosh, et al.; After sun reversal of DNA damage: enhancing skin repair; Mutation Research; vol. 571; No. 1-2; pp. 57-64; Apr. 2005.

Vallone, et al.; Start the Clock! Circadian Rhythms and Development; Developmental Dynamics; 236; pp. 142-155; 2007.

Sporl, Florian, et al.; A Circadian Clock in HaCaT Keratinocytes; The Journal of Investigative Dermatology; vol. 131, No. 2; pp. 338-348; Feb. 2011.

Reddy, et al.; Circadian clocks: neural and peripheral pacemakers that impact upon the cell division cycle.; Mutation Research; 574 (1-2):76-91; http://www.ncbi.nlm.nih.gov/pubmed/15914209?dopt=Abstract; Epub Apr. 15, 2005; Jul. 2005.

Tomonori Motokawa; Effect of Sophorae radix extract on melanocyte stimulating hormone; Fragrance Journal 2000; vol. 28, No. 9; pp. 38-44.

Supplemental European Search Report; EP10739214.4; Completion Date: Sep. 18, 2012; Date of Mailing: Sep. 25, 2012.

Hydrolyzed algin (http://www.md-7.com/D_1-5_2-60_4-463/hydrolyzed-algin.html; accessed Sep. 26, 2014.

Morselli, et al.; Spermidine and resveratrol induce autophagy by distinct pathways convergiing on the acetylproteome; J. Cell Biol.; vol. 192, No. 4; pp. 615-629; 2011.

PCT International Search Report; International Application No. PCT/US2013/058693; Completion Date: Jan. 13, 2014; Mailing Date: Jan. 13, 2014.

PCT Written Opinion of the International Searching Authority; Completion Date: Jan. 13, 2014; Mailing Date: Jan. 13, 2014.

Clarkson, et al.; The usefulness of tyrosinase in the immunohistochemical assessment of melanocytic lesions: a comparison of the novel T311 antibody (anti-tyrosinase) with S-100, HMB45, and A103 (anti-melan-A); Journal of Clinical Pathology; vol. 54, 2001; pp. 196-200.

Patterson, J.W., et al.; Hyperpigmented Scar Due to Minocycline Therapy; Continuing Medical Education; Cutis. vol. 74; Nov. 2004; pp. 293-209.

Wen, et al.; Erythropoietin structure-function relationships: high degree of sequence homology among mammals; Blood 1993, vol. 82, No. 5; The American Society of Hematology; pp. 1507-1516; http://www.bloodjournal.org/content/82/5/1507.

\* cited by examiner

```
                            SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
      or no amino acid
<220> FEATURE:
<221> NAME/KEY: misc_feature
<222> LOCATION: (5)
<223> OTHER INFORMATION: Xaa can be threonine or serine or no amino acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5

<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5
```

```
<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5
```

METHOD FOR REPAIRING DNA DAMAGE IN KERATINOCYTES

CROSS-REFERENCE TO RELATED APPLICATIONS

This application is a continuation of application Ser. No. 12/367,705 filed Feb. 9, 2009 now U.S. Pat. No. 8,193,155.

TECHNICAL FIELD

The invention is in the field of compositions for application to skin to repair, beautify, condition, and improve skin.

BACKGROUND OF THE INVENTION

It is well known that UV light, pollution, cigarette smoke and stress can be very detrimental to skin. The skin on the face is made up of keratinocytes. Exposure to such environmental aggressors causes damage to cellular DNA. For example, it is estimated that a single sun burn results in hundreds of thousands of DNA mutagenic base modifications such as T-T (thiamine-thiamine) dimmers; 8-oxo-7,8-dihydro-2'-deoxyguanosine (8-oxo-DG); 06MeG (06-methyl guanine); and 6-4PP (6-4 photoproducts) in affected cells. Fortunately, healthy keratinocytes have a natural internal mechanism for repairing these lesions. However, repair of DNA lesions takes time. For example, repair of TT dimers and 6-4PP damage formed by UVB exposure may take up to 48 and 8 hours respectively. Repair of 8-oxo-dG and 06MeG lesions due to UVA or UVB exposure, ozone, or smoke and pollution may take up to 2 hours. If DNA lesions are not repaired before cell division, the result is apoptosis, or cell death.

The body's natural circadian rhythms are synchronized such that during exposure to environmental aggressors—usually during daylight hours—certain genes in the cells are activated to produce proteins that protect the cells against damage. Then, during periods of rest, usually at night, gene activation is decreased with normal circadian rhythms.

Recently, genes associated with natural bodily circadian rhythms have been identified and include the CLOCK (Circadian Locomotor Output Cycles Kaput) gene and the PER1 (Period Homolog 1) gene, both of which encode proteins that regulate circadian rhythms. CLOCK and PER1 genes are also present in keratinocytes, and they promote synthesis of corresponding proteins which promote cellular viability and repair. However, with normal circadian rhythms, the genes are most activated during daylight hours. As the corresponding protein levels increase during the day, a feedback inhibition results and the genes are "turned off" as night time approaches.

Cosmetic products for application to skin prior to nightly rest are well known. Many of such products contain ingredients that help to promote the cellular repair process. For example, they may include DNA repair enzymes for improving the effectiveness of natural cellular DNA repair, humectant ingredients for maintaining keratinocyte hydration, moisturizing ingredients for improving skin barrier function, and so on. While these ingredients improve the ability of keratinocytes to repair during periods of nightly rest, there is always room for improvement.

It has been discovered that activation of CLOCK and PER1 genes present in keratinocytes results in synthesis of proteins that promote cellular viability, cellular longevity, inhibition of cellular damage due to environmental aggressors, and improved repair of DNA damage. Proteins produced by activation of CLOCK and PER1 genes are most often generated during the normal circadian rhythm cycle, that is during daylight, when the skin is most subjected to environmental aggressors.

It is an object of the invention to provide a method of inhibiting damage to human keratinocytes due to environmental aggressors by applying a composition comprising at least one keratinocyte CLOCK or PER1 gene activator and at least one DNA repair enzyme.

It is a further object of the invention to provide a method for repairing skin comprising applying to the skin a composition comprising at least one keratinocyte CLOCK or PER1 gene activator either alone or in combination with at least one DNA repair enzyme.

It is a further object of the invention to provide a composition for treating skin comprising at least one keratinocyte CLOCK or PER1 gene activator either alone or in combination with at least one DNA repair enzyme.

SUMMARY OF THE INVENTION

The invention is directed to a skin care composition comprising at least one keratinocyte CLOCK or PER1 gene activator and at least one DNA repair enzyme.

The invention is further directed to a method for inhibiting damage to human keratinocytes due to environmental aggressors by applying a composition comprising at least one keratinocyte CLOCK or PER1 gene activator and at least one DNA repair enzyme.

The invention is further directed to a method for repairing DNA damage in human keratinocytes by applying to such keratinocytes a composition comprising at least one CLOCK or PER1 gene activator and at least one DNA repair enzyme.

DETAILED DESCRIPTION

I. Definitions

Figure 1:
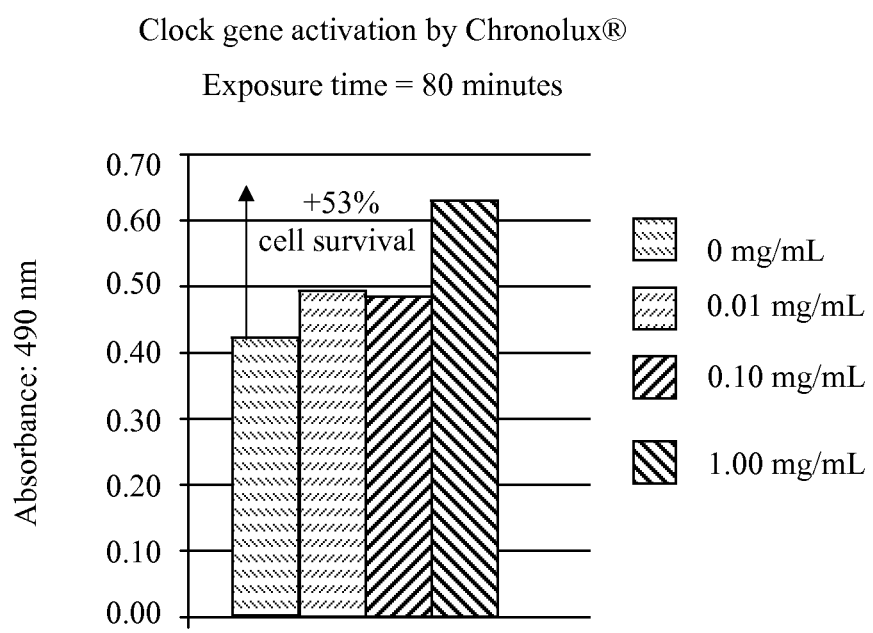
FIG. 1: demonstrates the ability of Chronolux® to activate keratinocyte CLOCK genes and thereby protect keratinocytes against UV induced stress.

All percentages mentioned herein are percentages by weight unless otherwise indicated.

"CLOCK gene activator" means an ingredient that activates one or more CLOCK genes present in keratinocytes to produce proteins that repair DNA damage, inhibit cellular damage cause by environmental aggressors, or otherwise improve the viability, strength, and/or longevity of keratinocytes. Included within the term "CLOCK gene" are the various components of the gene such as BMAL1, MOP3, and the like.

The term "DNA repair enzyme" means an enzyme that is operable to repair DNA base mutagenic damage. Such enzymes are often categorized by the type of DNA damage they repair, for example BER (base excision repair) enzymes, nucleotide excision repair (NER) enzymes; mismatch repair (MMR) enzymes; DNA helicases; DNA polymerases, and so on. For example, mutations such as 8-oxo-7,8-dihydro-2'-deoxyguanosine may be repaired by OGG1 (8-oxoGuanine glycosylase); T-T dimers which may be repaired by (Nucleotide excision repair (NER) Photolyase); 6-4 photoproducts (which may be repaired by NER); and 06-methyl guanine (which may be repaired by 06-alkyl guanine transferase (AGT)).

"PER1 gene activator" means an ingredient that activates one or more PER1 genes found in keratinocytes to produce proteins that repair DNA damage, inhibit cellular damage caused by environmental aggressors, or otherwise improve the viability, strength, and/or longevity of keratinocytes.

"Repair" means, with respect to skin, that keratinocyte viability, strength, and longevity are generally improved. This may occur, by, among other things, repair of damaged keratinocyte DNA, cellular hydration, moisturization, inhibition of keratinocyte damage due to UV light, smoke or other environmental aggressors.

II. CLOCK, PER1, Activator

The composition of the invention contains at least one CLOCK or PER1 keratinocyte gene activator. Suggested ranges are from about 0.000001 to about 40%, preferably from about 0.000005 to 35%, more preferably from about 0.00001 to 25%. Suitable CLOCK or PER1 activators may be present in the form of botanical extracts, polypeptides, peptides, amino acids, and the like.

A particularly preferred CLOCK and/or PER1 gene activator comprises a peptide of the formula (I):

$R_1-(AA)_n-X_1$—S-T-P—$X_2-(AA)_p-R_2$ where  is (SEQ ID No. 1) and:

$X_1$ represents a threonine, a serine, or is equal to zero,
$X_2$ represents an isoleucine, leucine, proline, valine, alanine, glycine, or is equal to zero,
AA represents any amino acid or derivative thereof, and n and p are whole numbers between 0 and 4,
$R_1$ represents the primary amine function of the N-terminal amino acid, either free or substituted by a protective grouping that may be chosen from either an acetyl group, a benzoyl group, a tosyl group, or a benzyloxycarbonyl group,
$R_2$ represents the hydroxyl group of the carboxyl function of the C-terminal amino acid, substituted by a protective grouping that may be chosen from either a $C_1$ to $C_{20}$ alkyl chain or an $NH_2$, NHY, or NYY group with Y representing a $C_1$ to $C_4$ alkyl chain,
wherein the sequence of general formula (I) comprises from about 3 to 13 amino acid residues,
said sequence of general formula (I) possibly containing substitutions of amino acids $X_1$ and $X_2$ with other chemically equivalent amino acids;
wherein the amino acids are:
Alanine (A)
Arginine (R)
Asparagine (N)
Aspartic Acid (D)
Cysteine (C)
Glutamic Acid (E)
Glutamine (Q)
Glycine (G)
Histidine (H)
Isoleucine (I)
Leucine (L)
Lysine (K)
Methionine (M)
Phenylalanine (F)
Proline (P)
Serine (S)
Threonine (T)
Tryptophan (W)
Tyrosine (Y)
Valine (V)

More preferred are peptides of the above formula as follows:

(SEQ ID No. 2)
Y-V-S-T-P-Y-N-$NH_2$

Tyr-Val-Ser-Thr-Pro-Tyr-Asn-$NH_2$ (SEQ ID NO. 3)
$NH_2$-V-S-T-P-E-$NH_2$ $NH_2$-Val-Ser-Thr-Pro-Glu-$NH_2$

S-T-P-$NH_2$

Ser-Thr-Pro-$NH_2$ (SEQ ID No. 4)
$NH_2$-L-H-S-T-P-P-$NH_2$ $NH_2$-Leu-His-Ser-Thr-Pro-Pro-$NH_2$ (SEQ ID No. 5)
$CH_3NHR$-H-S-T-P-E-$NH_2$ $CH_3$-NH-Arg-His-Ser-Thr-Pro-Glu-$NH_2$ (SEQ ID No. 6)
$CH_3NH$-H-S-T-P-E-$CH_3NH$ $CH_3$-NH-His-Ser-Thr-Pro-Glu-$CH_3$-NH

More preferred is the S-T-P—$NH_2$ peptide, SEQ ID No. 4, or mixtures thereof.

Most preferred is a peptide manufactured by ISP-Vinscience under the trademark Chronolux® having the INCI name Tripeptide-32.

III. DNA Repair Enzymes

The composition used in the method of the invention also contains at least one DNA repair enzyme. Suggested ranges are from about 0.00001 to about 35%, preferably from about 0.00005 to about 30%, more preferably from about 0.0001 to about 25% of one or more DNA repair enzymes.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of various species of macrococcus), lecithin, and water. Photosomes® comprises a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other suitable DNA repair enzymes include Endonuclease V, which may be produced by the denV gene of the bacteriophage T4. Also suitable are T4 endonuclease; $O^6$-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., E, coli uvrA/uvrB/uvrC endonuclease complex); APEX nuclease, which is a multi-functional DNA repair enzyme often referred to as "APE"; dihydrofolate reductase; terminal transferase; topoisomerase; $O^6$ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenoeytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP 1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MS114); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like.

Other examples of DNA repair enzymes include DNA helicases including such as ATP DNA helicase and so on.

The DNA repair enzymes may be present as components of botanical extracts, bacterial lysates, biological materials, and the like. For example, botanical extracts may contain DNA repair enzymes.

The compositions of the invention may contain one or more DNA repair enzymes. Preferably, the composition contains other ingredients that will provide a cosmetically or pharmaceutically acceptable product.

IV. Other Ingredients

The composition of the invention may be in the form of an emulsion, aqueous solution or dispersion, gel, or anhydrous composition. If in the form of an emulsion, it may be a water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

A. Humectants

The composition may contain one or more humectants. If present, they may range from about 0.1 to 75%, preferably from about 0.5 to 70%, more preferably from about 0.5 to 40%. Examples of suitable humectants include glycols, sugars, and the like. Suitable glycols are in monomeric or polymeric form and include polyethylene and polypropylene glycols such as PEG 4-10, which are polyethylene glycols having from 4 to 10 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the invention are $C_{1-6}$, preferably $C_2$ alkylene glycols, most particularly butylene glycol.

B. Sunscreens

It may also be desirable to include one or more sunscreens in the compositions of the invention. Such sunscreens include chemical UVA or UVB sunscreens or physical sunscreens in the particulate form. Inclusion of sunscreens in the compositions containing the whitening active ingredient will provide additional protection to skin during daylight hours and promote the effectiveness of the whitening active ingredient on the skin. If present, the sunscreens may range from about 0.1 to 50%, preferably from about 0.5 to 40%, more preferably from about 1 to 35%.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

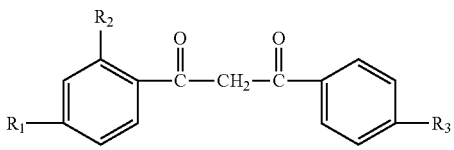

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercially available from Givaudan-Roure under the trademark Parsol® 1789, and Merck & Co. under the tradename Eusolex® 9020.

Other types of UVA sunscreens include dicamphor sulfonic acid derivatives, such as ecamsule, a sunscreen sold under the trade name Mexoryl®, which is terephthalylidene dicamphor sulfonic acid, having the formula:

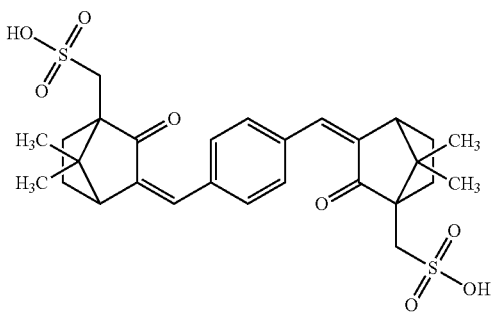 [SMILES: CC1(C)C2CCC1(CS(=O)(=O)O)C(=O)/C2=C\c1ccc(/C=C2\C(=O)C3(CS(=O)(=O)O)CCC2C3(C)C)cc1]

The composition may contain from about 0.001-20%, preferably 0.005-5%, more preferably about 0.005-3% by weight of the composition of UVA sunscreen. In the preferred embodiment of the invention the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 inn. A variety of UVB chemical sunscreens exist including alpha-cyano-beta,beta-diphenyl acrylic acid esters as set forth in U.S. Pat. No. 3,215,724, which is hereby incorporated by reference in its entirety. One particular example of an alpha-cyano-beta,beta-diphenyl acrylic acid ester is Octocrylene, which is 2-ethylhexyl 2-cyano-3,3-diphenylacrylate. In certain cases the composition may contain no more than about 10% by weight of the total composition of octocrylene. Suitable amounts range from about 0.001-10% by weight Octocrylene may be purchased from BASF under the tradename Uvinul® N-539.

Other suitable sunscreens include benzylidene camphor derivatives as set forth in U.S. Pat. No. 3,781,417, which is hereby incorporated by reference in its entirety. Such benzylidene camphor derivatives have the general formula:

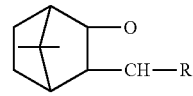

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

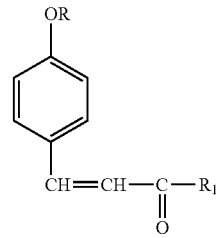

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol® MCX, or BASF under the tradename Uvinul® MC 80.

Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

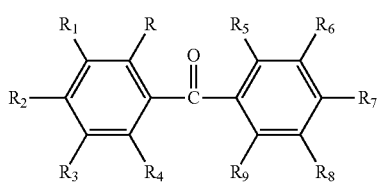

wherein R through $R_9$ are each independently H, OH, $NaO_3S$, $SO_3H$, $SO_3Na$, Cl, R″, OR″ where R″ is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

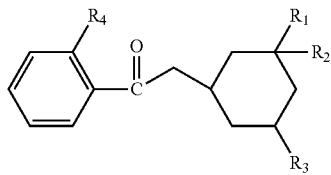

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomethyl salicylate (also known as Homosalate) or menthyl anthranilate. Homosalate is available commercially from Merck under the trademark Eusolex® HMS and menthyl anthranilate is commercially available from Haarmann & Reimer under the trademark Heliopan®. If present, the Homosalate should be found at no more than about 15% by weight of the total composition.

Various amino benzoic acid derivatives are suitable UVB absorbers including those having the general formula:

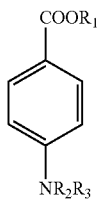

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof.

Generally, the amount of the UVB chemical sunscreen present may range from about 0.001-45%, preferably 0.005-40%, more preferably about 0.01-35% by weight of the total composition.

If desired, the compositions of the invention may be formulated to have a certain SPF (sun protective factor) values ranging from about 1-50, preferably about 2-45, most preferably about 5-30. Calculation of SPF values is well known in the art.

C. Surfactants

It may be desirable for the composition to contain one more surfactants, especially if in the emulsion form. However, such surfactants may be used if the compositions are solutions, suspensions, or anhydrous also, and will assist in dispersing ingredients that have polarity, for example pigments. Such surfactants may be silicone or organic based. The surfactants will also aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

1. Organic Nonionic Surfactants

The composition may comprise one or more nonionic organic surfactants. Suitable nonionic surfactants include alkoxylated alcohols or ethers, formed by the reaction of an alcohol with an alkylene oxide, usually ethylene or propylene oxide. Suitable alcohols include mono-, di-, or polyhydric short chain (C1-6) alcohols; aromatic or aliphatic saturated or unsaturated fatty (C12-40) alcohols, of cholesterol; and so on.

In one embodiment the alcohol is cholesterol, or an aromatic or aliphatic saturated or unsaturated fatty alcohol which may have from 6 to 40, preferably from about 10 to 30, more preferably from about 12 to 22 carbon atoms. Examples include oleyl alcohol, cetearyl alcohol, cetyl alcohol, stearyl alcohol, isostearyl alcohol, behenyl alcohol, and the like. Examples of such ingredients include Oleth 2-100; Steareth 2-100; Beheneth 5-30; Ceteareth 2-100; Ceteth 2-100; Choleth 2-100 wherein the number range means the number of repeating ethylene oxide units, e.g. Ceteth 2-100 means Ceteth where the number of repeating ethylene oxide units ranges from 2 to 100. Derivatives of alkoxylated alcohols are also suitable, such as phosphoric acid esters thereof.

Some preferred organic nonionic surfactants include Oleth-3, Oleth-5, Oleth-3 phosphate, Choleth-24; Ceteth-24; and so on.

Also suitable are alkoxylated alcohols formed with mono-, di-, or polyhydric short chain alcohols, for example those having from about 1 to 6 carbon atoms. Examples include glucose, glycerin, or alkylated derivatives thereof. Examples include glycereth 2-100; gluceth 2-100; methyl gluceth 2-100 and so on. More preferred are methyl gluceth-20; glycereth-26 and the like.

Other types of alkoxylated alcohols are suitable surfactants, including ethylene oxide polymers having varying numbers of repeating EO groups, generally referred to as PEG 12 to 200. More preferred are PEG-75, which is may be purchased from Dow Chemical under the trade name Carbowax PEG-3350.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with C6-30, preferably C12-22 fatty acids.

Examples of such ingredients include Polysorbates 20-85, sorbitan oleate, sorbitan sesquioleate, sorbitan palmitate, sorbitan sesquiisostearate, sorbitan stearate, and so on.

2. Silicone or Silane Surfactants

Also suitable are various types of silicone or silane-based surfactants. Examples include organosiloxanes substituted with ethylene oxide or propylene oxide groups such as PEG dimethicones which are dimethicones substituted with polyethylene glycols including those having the INCI names PEG-1 dimethicone; PEG-4 dimethicone; PEG-8 dimethicone; PEG-12 dimethicone; PEG-20 dimethicone; and so on.

Also suitable are silanes substituted with ethoxy groups or propoxy groups or both, such as various types of PEG methyl ether silanes such as bis-PEG-18 methyl ether dimethyl silane; and so on.

Further examples of silicone based surfactants include those having the generic names dimethicone copolyol; cetyl dimethicone copolyol; and so on.

D. Botanical Extracts

It may be desirable to incorporate one more additional botanical extracts into the composition. If present suggested ranges are from about 0.0001 to 20%, preferably from about 0.0005 to 15%, more preferably from about 0.001 to 10%. Suitable botanical extracts include extracts from plants (herbs, roots, flowers, fruits, seeds) such as flowers, fruits, vegetables, and so on, including yeast ferment extract, *Padina Pavonica* extract, *Thermus Thermophilis* ferment extract, *Camelina Saliva* seed oil, *Boswellia Serrata* extract, olive extract, *Acacia Dealbata* extract, *Acer Saccharinum* (sugar maple), *Acidopholus, Acorus, Aesculus, Agaricus, Agave, Agrimonia*, algae, aloe, citrus, *Brassica*, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza Glabra, Salix Nigra, Macrocycstis Pyrifera, Pyrus Mattis, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Panax Ginseng, Siegesbeckia Orientates, Fructus Mume, Ascophyllum Nodosum, Glycine Sofa* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata Peel, Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Kola Acuminata*, and mixtures thereof.

E. Biological Materials

Also suitable are various types of biological materials such as those derived from cells, fermented materials, and so on. If present such materials may range from about 0.001 to 30%, preferably from about 0.005 to 25%, more preferably from about 0.01 to 20%. Examples include fragments of cellular RNA or DNA, or probiotic microorganisms. Particularly preferred are RNA fragments.

F. Aqueous Phase Structuring Agent

In the case where the compositions are in the form of aqueous solutions, dispersions or emulsions, in addition to water the aqueous phase may contain one or more aqueous phase structuring agents, that is, an agent that increases the viscosity or, or thickens, the aqueous phase of the composition. This is particularly desirable when the composition is in the form of a serum or gel. Suitable ranges of aqueous phase structuring agent, if present, are from about 0.01 to 30%, preferably from about 0.1 to 20%, more preferably from about 0.5 to 15% by weight of the total composition. Examples of such agents include various acrylate based thickening agents, natural or synthetic gums, polysaccharides, and the like, including but not limited to those set forth below.

1. Polysaccharides

Polysaccharides may be suitable aqueous phase thickening agents. Examples of such polysaccharides include naturally derived materials such as agar, agarose, alicaligenes polysaccharides, algin, alginic acid, acacia gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, and so on.

2. Acrylate Polymers

Also suitable are different types of synthetic polymeric thickeners. One type includes acrylic polymeric thickeners comprised of monomers A and B wherein A is selected from the group consisting of acrylic acid, methacrylic acid, and mixtures thereof; and B is selected from the group consisting of a $C_{1-22}$ alkyl acrylate, a $C_{1-22}$ alkyl methacrylate, and mixtures thereof are suitable. In one embodiment the A monomer comprises one or more of acrylic acid or methacrylic acid, and the B monomer is selected from the group consisting of a $C_{1-10}$, most preferably $C_{1-4}$ alkyl acrylate, a $C_{1-10}$, most preferably $C_{1-4}$ alkyl methacrylate, and mixtures thereof. Most preferably the B monomer is one or more of methyl or ethyl acrylate or methacrylate. The acrylic copolymer may be supplied in an aqueous solution having a solids content ranging from about 10-60%, preferably 20-50%, more preferably 25-45% by weight of the polymer, with the remainder water. The composition of the acrylic copolymer may contain from about 0.1-99 parts of the A monomer, and about 0.1-99 parts of the B monomer. Acrylic polymer solutions include those sold by Seppic, Inc., under the tradename Capigel.

Also suitable are acrylic polymeric thickeners that are copolymer of A, B, and C monomers wherein A and B are as defined above, and C has the general formula:

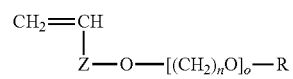

wherein Z is $—(CH_2)_m$; wherein m is 1-10, n is 2-3, o is 2-200, and R is a $C_{10-30}$ straight or branched chain alkyl. Examples of the secondary thickening agent above, are copolymers where A and B are defined as above, and C is CO, and wherein n, o, and R are as above defined. Examples of such secondary thickening agents include acrylates/steareth-20 methacrylate copolymer, which is sold by Rohm & Haas under the tradename Acrysol ICS-1.

Also suitable are acrylate based anionic amphiphilic polymers containing at least one hydrophilic unit and at least one allyl ether unit containing a fatty chain. Preferred are those where the hydrophilic unit contains an ethylenically unsaturated anionic monomer, more specifically a vinyl carboxylic acid such as acrylic acid, methacrylic acid or mixtures thereof, and where the allyl ether unit containing a fatty chain corresponds to the monomer of formula:

$$CH_2=CR'CH_2OB_nR$$

in which R' denotes H or $CH_3$, B denotes the ethylenoxy radical, n is zero or an integer ranging from 1 to 100, R denotes a hydrocarbon radical selected from alkyl, arylalkyl, aryl, alkylaryl and cycloalkyl radicals which contain from 8 to 30 carbon atoms, preferably from 10 to 24, and even more particularly from 12 to 18 carbon atoms. More preferred in this case is where R' denotes H, n is equal to 10 and R denotes a stearyl (C18) radical. Anionic amphiphilic polymers of this type are described and prepared in U.S. Pat. Nos. 4,677,152 and 4,702,844, both of which are hereby incorporated by reference in their entirety. Among these anionic amphiphilic polymers, polymers formed of 20 to 60% by weight acrylic acid and/or methacrylic acid, of 5 to 60% by weight lower alkyl methacrylates, of 2 to 50% by weight allyl ether containing a fatty chain as mentioned above, and of 0 to 1% by weight of a crosslinking agent which is a well-known copolymerizable polyethylenic unsaturated monomer, for instance diallyl phthalate, allyl (meth)acrylate, divinylbenzene, (poly) ethylene glycol dimethacrylate and methylenebisacrylamide. One commercial example of such polymers are crosslinked terpolymers of methacrylic acid, of ethyl acrylate, of polyethylene glycol (having 10 EO units) ether of stearyl alcohol or steareth-10, in particular those sold by the company Allied Colloids under the names SALCARE SC80 and SALCARE SC90, which are aqueous emulsions containing 30% of a crosslinked terpolymer of methacrylic acid, of ethyl acrylate and of steareth-10 alkyl ether (40/50/10).

Also suitable are acrylate copolymers such as Polyacrylate-3 which is a copolymer of methacrylic acid, methylmethacrylate, methylstyrene isopropylisocyanate, and PEG-40 behenate monomers; Polyacrylate-10 which is a copolymer of sodium acryloyldimethyltaurate, sodium acrylate, acrylamide and vinyl pyrrolidone monomers; or Polyacrylate-11, which is a copolymer of sodium acryloyldimethylacryloyldimethyl taurate, sodium acrylate, hydroxyethyl acrylate, lauryl acrylate, butyl acrylate, and acrylamide monomers.

Also suitable are crosslinked acrylate based polymers where one or more of the acrylic groups may have substituted long chain alkyl (such as 6-40, 10-30, and the like) groups, for example acrylates/$C_{10-30}$ alkyl acrylate crosspolymer which is a copolymer of C10-30 alkyl acrylate and one or more monomers of acrylic acid, methacrylic acid, or one of their simple esters crosslinked with the allyl ether of sucrose or the allyl ether of pentaerythritol. Such polymers are commonly sold under the Carbopol or Pemulen tradenames and have the CTFA name carbomer.

Also suitable are acrylate based polymeric thickeners sold by Clariant under the Aristoflex trademark such as Aristoflex AVC, which is ammonium acryloyldimethyltaurate/VP copolymer; Aristoflex AVL which is the same polymer has found in AVC dispersed in mixture containing caprylic/capric triglyceride, trilaureth-4, and polyglyceryl-2 sesquiisostearate; or Aristoflex HMB which is ammonium acryloyldimethyltaurate/beheneth-25 methacrylate crosspolymer, and the like.

3. High Molecular Weight PEG or Polyglycerins

Also suitable as the aqueous phase thickening agents are various polyethylene glycols (PEG) derivatives where the degree of polymerization ranges from 1,000 to 200,000. Such ingredients are indicated by the designation "PEG" followed by the degree of polymerization in thousands, such as PEG-45M, which means PEG having 45,000 repeating ethylene oxide units. Examples of suitable PEG derivatives include PEG 2M, 5M, 7M, 9M, 14M, 20M, 23M, 25M, 45M, 65M, 90M, 115M, 160M, 180M, and the like.

Also suitable are polyglycerins which are repeating glycerin moieties where the number of repeating moieties ranges from 15 to 200, preferably from about 20-100. Examples of suitable polyglycerins include those having the CFTA names polyglycerin-20, polyglycerin-40, and the like.

G. Oils

In the event the compositions of the invention are in emulsion form, the composition will comprise an oil phase. Oily ingredients are desirable for the skin moisturizing and protective properties. Suitable oils include silicones, esters, vegetable oils, synthetic oils, including but not limited to those set forth herein. The oils may be volatile or nonvolatile, and are preferably in the form of a pourable liquid at room temperature. The term "volatile" means that the oil has a measurable vapor pressure, or a vapor pressure of at least about 2 mm. of mercury at 20° C. The term "nonvolatile" means that the oil has a vapor pressure of less than about 2 mm. of mercury at 20° C.

1. Volatile Oils

Suitable volatile oils generally have a viscosity ranging from about 0.5 to 5 centistokes 25° C. and include linear silicones, cyclic silicones, paraffinic hydrocarbons, or mixtures thereof.

(a). Volatile Silicones

Cyclic silicones are one type of volatile silicone that may be used in the composition.

Such silicones have the general formula:

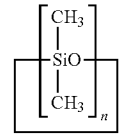

where n=3-6, preferably 4, 5, or 6.

Also suitable are linear volatile silicones, for example, those having the general formula:

where n=0, 1, 2, 3, 4, or 5, preferably 0, 1, 2, 3, or 4.

Cyclic and linear volatile silicones are available from various commercial sources including Dow Corning Corporation and General Electric. The Dow Corning linear volatile silicones are sold under the tradenames Dow Corning 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

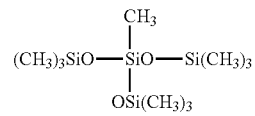

Methyl trimethicone may be purchased from Shin-Etsu Silicones under the tradename TMF-1.5, having a viscosity of 1.5 centistokes at 25° C.

(b). Volatile Paraffinic Hydrocarbons

Also suitable as the volatile oils are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of 70-225, preferably 160 to 190 and a boiling point range of 30 to 320, preferably 60 to 260° C., and a viscosity of less than about 10 cst. at 25° C. Such paraffinic hydrocarbons are available from EXXON under the ISOPARS trademark, and from the Permethyl Corporation. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

2. Non-Volatile Oils

A variety of nonvolatile oils are also suitable for use in the compositions of the invention. The nonvolatile oils generally have a viscosity of greater than about 5 to 10 centistokes at 25° C., and may range in viscosity up to about 1,000,000 centipoise at 25° C. Examples of nonvolatile oils include, but are not limited to:

(a). Esters

Suitable esters are mono-, di-, and triesters. The composition may comprise one or more esters selected from the group, or mixtures thereof.

(i) Monoesters

Monoesters are defined as esters formed by the reaction of a monocarboxylic acid having the formula R—COOH, wherein R is a straight or branched chain saturated or unsaturated alkyl having 2 to 45 carbon atoms, or phenyl; and an alcohol having the formula R—OH wherein R is a straight or branched chain saturated or unsaturated alkyl having 2-30 carbon atoms, or phenyl. Both the alcohol and the acid may be substituted with one or more hydroxyl groups. Either one or both of the acid or alcohol may be a "fatty" acid or alcohol, and may have from about 6 to 30 carbon atoms, more preferably 12, 14, 16, 18, or 22 carbon atoms in straight or branched chain, saturated or unsaturated form. Examples of monoester oils that may be used in the compositions of the invention include hexyl laurate, butyl isostearate, hexadecyl isostearate, cetyl palmitate, isostearyl neopentanoate, stearyl heptanoate, isostearyl isononanoate, steary lactate, stearyl octanoate, stearyl stearate, isononyl isononanoate, and so on.

(ii). Diesters

Suitable diesters are the reaction product of a dicarboxylic acid and an aliphatic or aromatic alcohol or an aliphatic or aromatic alcohol having at least two substituted hydroxyl groups and a monocarboxylic acid. The dicarboxylic acid may contain from 2 to 30 carbon atoms, and may be in the straight or branched chain, saturated or unsaturated form. The dicarboxylic acid may be substituted with one or more hydroxyl groups. The aliphatic or aromatic alcohol may also contain 2 to 30 carbon atoms, and may be in the straight or branched chain, saturated, or unsaturated form. Preferably, one or more of the acid or alcohol is a fatty acid or alcohol, i.e. contains 12-22 carbon atoms. The dicarboxylic acid may also be an alpha hydroxy acid. The ester may be in the dimer or trimer form. Examples of diester oils that may be used in the compositions of the invention include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

(iii). Triesters

Suitable triesters comprise the reaction product of a tricarboxylic acid and an aliphatic or aromatic alcohol or alternatively the reaction product of an aliphatic or aromatic alcohol having three or more substituted hydroxyl groups with a monocarboxylic acid. As with the mono- and diesters mentioned above, the acid and alcohol contain 2 to 30 carbon atoms, and may be saturated or unsaturated, straight or branched chain, and may be substituted with one or more hydroxyl groups. Preferably, one or more of the acid or alcohol is a fatty acid or alcohol containing 12 to 22 carbon atoms. Examples of triesters include esters of arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Esters suitable for use in the composition are further described in the C.T.F.A. Cosmetic Ingredient Dictionary and Handbook, Eleventh Edition, 2006, under the classification of "Esters", the text of which is hereby incorporated by reference in its entirety.

(b). Hydrocarbon Oils

It may be desirable to incorporate one or more nonvolatile hydrocarbon oils into the composition. Suitable nonvolatile hydrocarbon oils include paraffinic hydrocarbons and olefins, preferably those having greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof. In one preferred embodiment such hydrocarbons have a molecular weight ranging from about 300 to 1000 Daltons.

(c). Glyceryl Esters of Fatty Acids

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink seed oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups, glyceryl stearate, diglyceryl diisostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(d). Nonvolatile Silicones

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone.

For example, such nonvolatile silicones may have the following general formula:

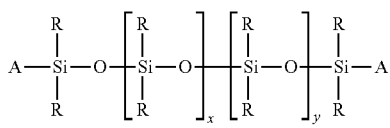

wherein R and R' are each independently $C_{1-30}$ straight or branched chain, saturated or unsaturated alkyl, phenyl or aryl, trialkylsiloxy, and x and y are each independently 1-1,000,000; with the proviso that there is at least one of either x or y, and A is alkyl siloxy endcap unit. Preferred is where A is a methyl siloxy endcap unit; in particular trimethylsiloxy, and R and R' are each independently a $C_{1-30}$ straight or branched chain alkyl, phenyl, or trimethylsiloxy, more preferably a $C_{1-22}$ alkyl, phenyl, or trimethylsiloxy, most preferably methyl, phenyl, or trimethylsiloxy, and resulting silicone is dimethicone, phenyl dimethicone, diphenyl dimethicone, phenyl trimethicone, or trimethylsiloxyphenyl dimethicone. Other examples include alkyl dimethicones such as cetyl dimethicone, and the like wherein at least one R is a fatty alkyl ($C_{12}$, $C_{14}$, $C_{16}$, $C_{18}$, $C_{20}$, or $C_{22}$), and the other R is methyl, and A is a trimethylsiloxy endcap unit, provided such alkyl dimethicone is a pourable liquid at room temperature. Phenyl trimethicone can be purchased from Dow Corning Corporation under the tradename 556 Fluid. Trimethylsiloxyphenyl dimethicone can be purchased from Wacker-Chemie under the tradename PDM-1000. Cetyl dimethicone, also referred to as a liquid silicone wax, may be purchased from Dow Corning as Fluid 2502, or from DeGussa Care & Surface Specialties under the trade names Abil Wax 9801, or 9814.

H. Vitamins and Antioxidants

It may be desirable to incorporate one or more vitamins or antioxidants in the compositions. If present, suggested ranges are from about 0.001 to 20%, preferably from about 0.005 to 15%, more preferably from about 0.010 to 10%. Preferably such vitamins, vitamin derivatives and/or antioxidants are operable to scavenge free radicals in the form of singlet oxygen. Such vitamins may include tocopherol or its derivatives such as tocopherol acetate, tocopherol ferulate; ascorbic acid or its derivatives such as ascorbyl palmitate, magnesium ascorbyl phosphate; Vitamin A or its derivatives such as retinyl palmitate; or vitamins D, K, B, or derivatives thereof.

I. Preferred Compositions

Preferred compositions are in the aqueous solution or emulsion form and contain at least one nonionic organic surfactant, at least one chemical sunscreen, at least one CLOCK or PER1 gene activator, at least one DNA repair enzyme, at least one additional botanical extract, and at least one oil.

More preferred is where the composition the nonionic organic surfactant is an alkoxylated alcohol, the chemical sunscreen is a UVB sunscreen, the CLOCK or PER1 keratinocyte gene activator is Tripeptide-32, the DNA repair enzyme is a mixture of *Arabidopsis Thaliana* extract, *Micrococcus* lysate, *Bifida* Ferment lysate, *Lactobacillus* ferment, and Plankton extract, and the at least one oil is an organic ester or hydrocarbon.

V. The Method

The invention is also directed to method for inhibiting damage to human keratinocytes, preferably facial keratinocytes, which occurs in response to environmental aggressors by applying a composition comprising at least one keratinocyte CLOCK or PER1 gene activator and at least one DNA repair enzyme; and a method for repairing DNA damage to human keratinocytes due to such aggressors by applying the composition of the invention. The keratinocyte damage that is inhibited and/or repaired includes damage from UV light, cigarette smoke, environmental pollution or toxins, stress, and the like. Application of the composition of the invention will repair damaged DNA in keratinocytes due to any of the above conditions, and will also improve keratinocyte viability and longevity.

In the method of the invention, the composition may be applied to skin one or more times per day. For example, the composition may be applied to skin in the morning prior to beginning daily activities and/or at night prior to retiring. The composition may be applied as part of a regimen; that is, the skin is cleansed and treated with toner, after which the composition of the invention is applied. The composition may be part of a kit containing a cleanser, toner, and the composition of the invention.

Preferably the composition is applied to the face and/or neck and décolletage prior to retiring to repair DNA damaged keratinocytes and provide general improvement of the skin. When applied prior to retiring, the CLOCK and PER1 gene activators in the composition will activate keratinocyte genes at a time when they would be less active or inactive in the normal circadian rhythm cycle. In turn, such activation of the CLOCK and PER1 genes at this time promotes improved repair of DNA damaged keratinocytes. This in turn promotes cellular viability and longevity. Thus, maximum repair of human keratinocytes is accomplished. Combining the CLOCK and PER1 gene activators with DNA repair enzymes in a composition used to treat facial skin at night prior to retiring maximizes the keratinocyte repair due to DNA damage and also promotes cellular viability, longevity, and health.

The invention will be further described in connection with the following examples which are set forth for the purposes of illustration only.

Example 1

A skin treatment composition was prepared as follows:

| Ingredient | w/w % |
| --- | --- |
| Oleth-3 phosphate | 0.45 |
| Oleth-3 | 0.35 |
| Oleth-5 | 0.24 |
| Butylene glycol | 0.20 |
| Squalane | 0.50 |
| BHT | 0.10 |
| Ethylhexyl methoxycinnamate | 0.10 |
| Choleth-24/ceteth-24 | 0.10 |
| Triethanolamine | 0.11 |
| Retinyl palmitate/*zea mays* (corn) oil/BHT/BHA | 0.10 |
| Butylene glycol | 1.10 |
| Chamomile | 0.03 |
| Bisabolol | 0.10 |
| Water | QS |
| Methyl paraben | 0.46 |
| PEG-75 | 4.00 |
| Bis-PEG-18 methyl ether dimethyl silane | 2.00 |
| Glycereth-26 | 1.00 |
| Methyl gluceth-20 | 4.00 |
| Trisodium EDTA | 0.10 |
| Pantethine | 0.14 |
| Caffeine | 0.05 |
| Xanthan gum | 0.075 |
| Carbomer | 0.26 |
| Triethanolamine | 0.50 |
| Phenoxyethanol | 0.70 |
| Benzyl alcohol | 0.10 |
| Bifida ferment lysate | 9.40 |
| Water/bifida ferment lysate/hydrogenated lecithin | 3.00 |

-continued

| Ingredient | w/w % |
|---|---|
| Butylene glycol/water/*Cola Acuminata* extract | 3.00 |
| Sodium ribonucleic acid | 0.01 |
| Water/butylene glycol/tripeptide-32 | 0.20 |
| Lactobacillus ferment/lecithin/water | 0.05 |
| Water/*Arabidopsis Thaliana* extract/lecithin | 0.05 |
| Phenoxyethanol | 0.02 |
| Sodium hyaluronate | 0.01 |
| FD&C Red No. 4 (1% aqueous solution with butylene glycol) | 0.04 |
| FD&C Yellow No. 5 (1% aqueous solution with butylene glycol) | 0.09 |
| D&C Green No. 5 (0.1% solution with butylene glycol) | 0.001 |

The composition was prepared by combining the ingredients and mixing well to form a liquid. The composition was stored in brown glass bottles.

Example 2

CLOCK and PER1 genes in human keratinocytes were activated by exposing the keratinocytes to Chronolux®, then exposing the cells to UV light to ascertain the impact of gene activation on keratinocytes exposed to UV light.

Normal human keratinocytes were cultured in Epilife® Medium containing Human Keratinocyte Growth Supplement (S001-5) (Invitrogen—Gibco Cell Culture, Portland, Oreg.). The cells were cultured into 96-well plates (Costar®) and pretreated with 0, 0.01, 0.1 and 1 mg/ml Chronolux® powder diluted in the Epilife® medium and incubated overnight at 37° C. in 5% $CO_2$. After 24 hours the media was aspirated and the keratinocytes washed once in Dulbecco's phosphate buffered saline (PBS). 100 µl of PBS was added to each well and the cells were subjected to Solar Simulated UV irradiation at 80 minutes of exposure. After the irradiation the PBS was removed and the keratinocytes were post treated with Chronolux® again at the same dilutions as before and incubated overnight at 37° C. in 5% $CO_2$.

Cells were assayed for viability the next day utilizing MTS reagent (CellTiter96, Promega), 100 ul per well. Absorbance readings were taken on the SpectraMax190 spectrophotometer (Molecular Devices) at 490 nm following an approximate two hour incubation at 37° C. in 5% $CO_2$.

The results are set forth in FIG. 1 and show that cell survival increased significantly after UV exposure when cells were treated with varying doses of Chronolux® prior to such UV exposure. Thus, exposure of human keratinocytes to Tripeptide-32 prior to UV exposure significantly improves cell survival upon exposure to UV light.

Example 3

Human keratinocytes same conce as prior exp were treated with Chronolux® in varying dilutions and exposed to UV light to ascertain the impact of Chronolux® on inhibiting UV damage in keratinocytes.

Normal human keratinocytes (HEKn) were cultured in Epilife® Medium with Human Keratinocyte Growth Supplement. The cells were sub-cultured at approximately 70% confluence in a 96-well plate and allowed to incubate overnight at 37° C.

Keratinocytes were pretreated with 1 mg/ml solution of Chronolux® (1 mg/ml aqueous solution), and with a mixture containing 1 mg/ml Chronolux®, 10% *Bifidus* Ferment lysate, 1% Adasomes® (a mixture of 98.26% water, 0.5% lecithin, 0.5% *Lactobacillus* ferment, 0.375% phenoxyethanol, 0.04% sorbic acid, and 0.325% caprylyl glycol) and 1% Roxisomes® (a mixture of 98% water, 0.5% lecithin, and 0.1% phenoxyethanol) in aqueous solution. This mixture was tested undiluted and at dilutions of 1:2, 1:4, and 1:8.

The treated keratinocytes were incubated overnight at 37° C. in 5% $CO_2$. After 24 hours, the cells were aspirated and keratinocytes were washed once in PBS, after which 100 µl of PBS was added to each well. The cells were UVB irradiated at 150 mJ/cm². After the irradiation, the PBS was removed; the keratinocytes were again pretreated as previously set forth and incubated overnight at 37° C. in 5% $CO_2$.

Cells were assayed for viability the next day utilizing MTS reagent (CellTiter96, Promega). Absorbance readings were taken on the SpectraMax190 spectrophotometer (Molecular Devices) at 490 nm following an approximate two hour incubation at 37° C.; 5% $CO_2$.

Figure 2:
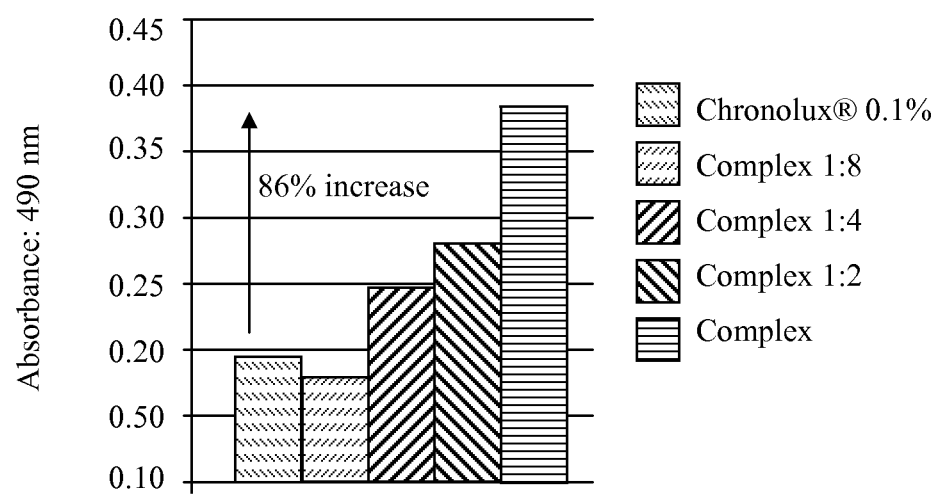
FIG. 2: demonstrates that keratinocytes survival and viability are improved when keratinocytes are treated with the composition of the invention and then exposed to UV light.

The results are set forth in FIG. 2 and demonstrate the mixture of Tripeptide-32, *Bifidus* Ferment Lysate, Adasomes® and Roxisomes® provided a dose dependent increase in protection against UVB stress, e.g. cell viability and longevity. The undiluted mixture provided an 86% increase in cell viability compared to the Chronolux® alone at radiation of 150 mJ/cm² UVB. It can be concluded that when human keratinocytes were treated with the mixture, it provided a synergistic effect that significantly increased protection against UVB stress.

Example 4

Human keratinocytes were exposed to a composition of the invention (Chronolux® 0.1%, *Bifidus* Ferment Lysate 12.4%, Adasomes® 0.05%, Roxisomes® 0.05%; referred to as "New ANR") and a composition containing only *Bifidus* Ferment Lysate (21.4%; referred to as "Previous ANR") then irradiated with UVB light to determine how effectively the compositions inhibited keratinocyte DNA damage due to UVB light.

Normal human keratinocytes (HEKn) were cultured in Epilife® Medium with Human Keratinocyte Growth Supplement. The cells were sub-cultured at approximately 70% confluence in a 96-well plate (Costar) and allowed to incubate overnight at 37° C.

Keratinocytes were pretreated with *Bifidus* Ferment Lysate (12.4% aqueous solution) by itself (Previous ANR), and a mixture of *Bifidus* Ferment Lysate (12.4%), Chronolux® (1 mg/ml), Adasomes® (0.05%) and Roxisomes® (0.05%) diluted in Epilife® media.

Treated keratinocytes were incubated at 37° C. in 5% $CO_2$. After 24 hours, cells were aspirated and keratinocytes were washed once in Dulbecco's PBS after which 100 µl of PBS was added to each well. The cells were subjected to UVB irradiation at 150 & 200 mJ/cm² UVB. After the irradiation, the PBS was removed. The pretreatment was repeated and the keratinocytes incubated for approximately 30 his at 37° C. in 5% $CO_2$.

Cells were assayed for viability the next day utilizing MTS reagent (CellTiter96, Promega). Absorbance readings were taken on the SpectraMax190 spectrophotometer (Molecular Devices) at 490 nm following an approximate two hour incubation at 37° C.; 5% $CO_2$.

Figure 3:
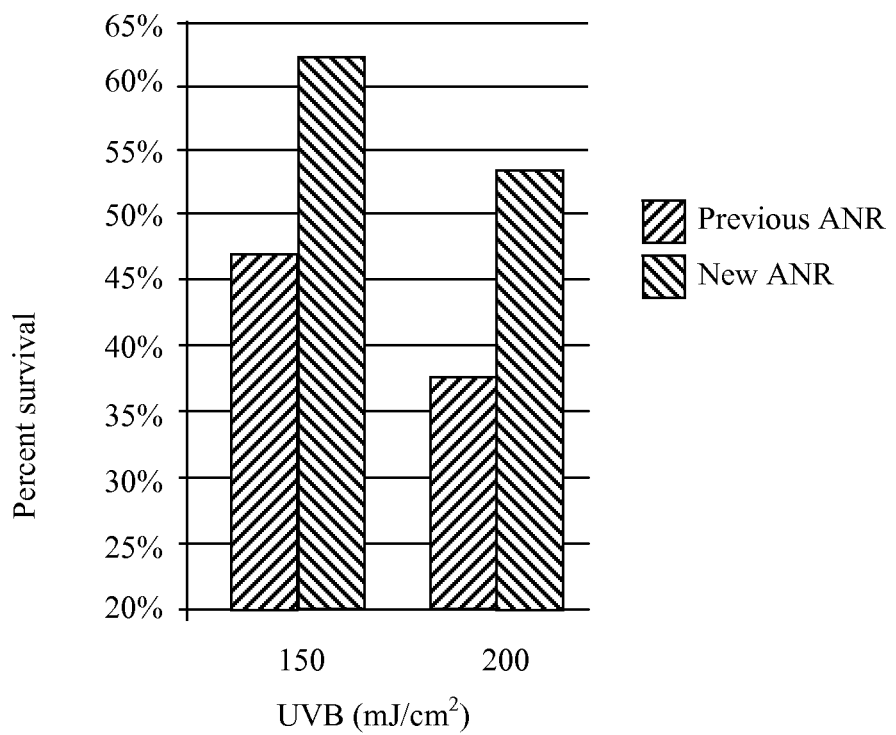
FIG. 3: demonstrates the improvement in keratinocyte survival between a composition containing the combination of at least one CLOCK or PER1 gene activator and at least one DNA repair enzyme is compared with a composition containing DNA repair enzymes alone.

The results are set forth in FIG. 3 and demonstrate an increase of approximately 15% cell survival observed at both 150 and 200 µmJ/cm² UVB in the cells treated with the new ANR complex when compared to the previous ANR. It can be concluded that the new ANR complex provided significant more protection against UVB stress when compare to the previous version. The addition of the Chronolux®, Adasomes®, and Roxisomes® to the *Bifidus* Extract provided a significant increase in cell survival over the *Bifidus* alone found in the previous ANR complex.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A method for inhibiting UV damage in keratinocytes by applying to the skin of a human subject in need thereof a cosmetic composition comprising at least one CLOCK or PER1 gene activator and inactivated bacterial lysates from *Bifido* bacterium.

2. The method of claim 1 wherein the CLOCK or PER1 gene activator is a peptide having from about 3 to 13 amino acid residues and of the formula (I) (SEQ ID NO:1):

$$R_1\text{-}(AA)_n\text{-}X_1\text{-}Ser\text{-}Thr\text{-}Pro\text{-}X_2\text{-}(AA)_p\text{-}R_2$$

wherein:
- $X_1$ represents threonine, serine, or is a covalent bond,
- $X_2$ represents an isoleucine, leucine, proline, valine, alanine, glycine, or is a covalent bond,
- AA represents any amino acid or derivative thereof, and n and p are whole numbers between 0 and 4,
- $R_1$ is bonded to the N-terminal amino acid of the peptide and is a hydrogen atom or a substituent selected from benzoyl group, a tosyl group, or a benzyloxycarbonyl,
- $R_2$ is bonded to the carboxyl group of the C-terminal amino acid of formula I, and is selected from the group consisting of hydroxyl, a $C_1$ to $C_{20}$ alkoxy, $NH_2$, NHY, or N(Y)Y group with Y a $C_1$ to $C_4$ alkyl chain.

3. The method of claim 1 wherein the CLOCK or PER1 gene activators are selected from the group consisting of:

Ser-Thr-Pro-$NH_2$ (SEQ ID No: 2)
Tyr-Val-Ser-Thr-Pro-Tyr-Asn-$NH_2$ (SEQ ID No: 3)
Val-Ser-Thr-Pro-Glu-$NH_2$ (SEQ ID No: 4)
Leu-His-Ser-Thr-Pro-Pro-$NH_2$ (SEQ ID No: 5)
$H_3$C-Arg-His-Ser-Thr-Pro-Glu-$NH_2$ (SEQ ID No: 6)
$H_3$C-His-Ser-Thr-Pro-Glu-$CH_3$-$NH_2$ and mixtures thereof.

4. The method of claim 3 wherein the CLOCK or PER1 gene activators are selected from:

Ser-Thr-Pro-$NH_2$ (SEQ ID No: 4)
Leu-His-Ser-Thr-Pro-Pro-$NH_2$ and mixtures thereof.

5. The method of claim 2 wherein the CLOCK or PER1 gene activator is a peptide having the formula Ser-Thr-Pro-$NH_2$.

6. The method of claim 2 wherein the CLOCK or PER1 gene activator is a peptide having the formula: Ser-Thr-Pro-$NH_2$ and the DNA repair enzyme is selected from the group consisting of:
- base excision repair (BER) enzymes,
- nucleotide excision repair (NER) enzymes,
- DNA polymerases,
- DNA helicases,
- Mismatch repair (MMR) enzymes;
- and mixtures thereof.

7. The method of claim 2 wherein the CLOCK or PER1 gene activator is a peptide having the formula Ser-Thr-Pro-$NH_2$ and the inactivated bacterial lysate from *Bifido* bacterium is *Bifida* ferment lysate.

8. The method of claim 1 wherein the composition further comprises at least one additional botanical extract.

9. The method of claim 1 wherein the composition further comprises at least one free radical scavenger operable to inactivate singlet oxygen in skin keratinocytes.

10. The method of claim 1 wherein the composition further comprises at least one aqueous phase structuring agent comprising a polysaccharide, an acrylic polymer, or mixtures thereof.

11. The method of claim 1 wherein the composition further comprises at least one vitamin or vitamin derivative.

12. The method of claim 1 wherein the cosmetic composition is in the form of a solution, dispersion, suspension, or emulsion.

13. The method of claim 1 wherein the composition is applied to the skin prior to nightly rest.

14. The method of claim 1 wherein the composition is applied to the skin as part of a regimen comprised of cleansing, toning, and application of the composition to the skin.

15. The method of claim 1 wherein the keratinocytes are facial keratinocytes.

16. The method of claim 1 wherein the composition is applied to the skin twice per day.

17. A method for inhibiting UV damage in skin comprising applying to the skin of a human subject in need thereof a composition comprising at least one CLOCK or PER1 gene activator and a DNA repair enzyme contained in one or more of the following:

*Arabidopsis Thaliana* extract either alone or in admixture with lecithin and water;
*Lactobacillus* ferment,
*Micrococcus* lysate,
Plankton extract,
*Bifida* ferment lysate; and
mixtures thereof.

18. The method of claim 17 wherein the DNA repair enzyme is contained in inactivated bacterial lysates of *Bifido* bacterium.

19. The method of claim 17 wherein the DNA repair enzyme is contained in *Micrococcus* lysate.

20. The method of claim 17 wherein the DNA repair enzyme is contained in *Lactobacillus* ferment.

* * * * *